(12) United States Patent
Siddiqui

(10) Patent No.: US 10,123,965 B2
(45) Date of Patent: Nov. 13, 2018

(54) FORMULATIONS, METHODS AND DEVICES FOR PERIORBITAL SKIN REJUVENATION

(71) Applicant: Younique, LLC, Lehi, UT (US)

(72) Inventor: Mukhtar Siddiqui, Lehi, UT (US)

(73) Assignee: YOUNIQUE, LLC, Lehi, UT (US)

(*) Notice: Subject to any disclaimer, the term of this patent is extended or adjusted under 35 U.S.C. 154(b) by 121 days.

(21) Appl. No.: 15/329,036

(22) PCT Filed: Jul. 30, 2014

(86) PCT No.: PCT/US2014/048927
§ 371 (c)(1),
(2) Date: Jan. 25, 2017

(87) PCT Pub. No.: WO2016/018315
PCT Pub. Date: Feb. 4, 2016

(65) Prior Publication Data
US 2017/0231899 A1    Aug. 17, 2017

(51) Int. Cl.
| | |
|---|---|
| *A61K 8/31* | (2006.01) |
| *A61K 8/37* | (2006.01) |
| *A61K 8/67* | (2006.01) |
| *A61K 8/97* | (2017.01) |
| *A61K 8/35* | (2006.01) |
| *A61Q 19/08* | (2006.01) |
| *A45D 34/04* | (2006.01) |

(52) U.S. Cl.
CPC ............. *A61K 8/97* (2013.01); *A45D 34/04* (2013.01); *A61K 8/31* (2013.01); *A61K 8/355* (2013.01); *A61K 8/37* (2013.01); *A61K 8/375* (2013.01); *A61K 8/676* (2013.01); *A61K 8/678* (2013.01); *A61Q 19/08* (2013.01); *A61K 2800/30* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 2005/0186169 A1 | 8/2005 | Charbit | |
| 2007/0003536 A1* | 1/2007 | Zimmerman | ............ A61K 8/35 424/94.4 |
| 2007/0092469 A1 | 4/2007 | Jacobs | |
| 2012/0045405 A1 | 2/2012 | Gilman et al. | |

FOREIGN PATENT DOCUMENTS

| | | |
|---|---|---|
| JP | 10095724 A * | 4/1998 |
| KR | 10-20120139328 | 12/2012 |
| WO | 2009127058 | 10/2009 |
| WO | 2014054882 | 4/2014 |
| WO | 2016018315 | 2/2016 |

OTHER PUBLICATIONS

Naolys, ("All Even Sweet Iris", Naolys, available at www.naolys.com/media/all_even_sweet_iris_en.pdf, copyright 2014, webcapture indicating availability as of Jan. 27, 2014 provided). (Year: 2014).*
EP; Extended European Search Report dated Mar. 29, 2018 in Application No. 14898831.4.
Database GNPD [Online] "Ideal Eyes Anti-Fatigue Integral Serum," Mintel; XP002776129, Database accession No. 2220270 (2014).
PCT; International Search Report and Written Opinion dated Apr. 27, 2015 in Application No. PCT/US2014/048927.
PCT; International Preliminary Report on Patentability dated Feb. 9, 2017 in Application No. PCT/US2014/048927.
EPO; European Search Report dated Dec. 14, 2017 in Application No. 14898831.4.
Amyris, "Neossance Squalane," Analytical Data (2014).
Barnet Products Corporation, "BV-OSC A Stable, Oil-Soluble Form of Vitamin C," (2004).
Barnet Products Corporation, "BV-OSC" (2013).
AMA Laboratories, Inc., "Cell Renewal Study," (2014).
AMA Laboratories, Inc., "Comedogenic Potential on Human Subjects," (2013).
Naolys, "All Even Sweet Iris, Increasing Skin Density," (2010).
Naolys, "Assessment of the Anit-Wrinkle Effect of a Cosmetic Product on Human," (2012).
Saecker, Christine, "All-Q Plus to Unveil the Secret of Beauty," DSM Nutritional Products (2007).
Amyris, "Renewable Squalane Highly Pure and Reliable Source," (2011).

\* cited by examiner

*Primary Examiner* — Louise Humphrey
*Assistant Examiner* — Charles Zoltan Constantine
(74) *Attorney, Agent, or Firm* — Snell & Wilmer L.L.P.

(57) ABSTRACT

The present disclosure provides formulations, methods and devices for periorbital skin rejuvenation. A periorbital skin serum in accordance with the present disclosure comprises squalane (sugarcane derived), vitamin E (tocopheryl acetate), vitamin C (tetrahexyldecyl ascorbate), and ubiquinone (coenzyme Q10, oxidized form).

6 Claims, 2 Drawing Sheets

FORMULATIONS, METHODS AND DEVICES FOR PERIORBITAL SKIN REJUVENATION

CROSS-REFERENCE TO RELATED APPLICATIONS

This application is a U.S. national phase filing under 35 U.S.C. § 371 of PCT/US2014/048927 filed Jul. 30, 2014 entitled "FORMULATIONS, METHODS AND DEVICES FOR PERIORBITAL SKIN REJUVENATION, which is incorporated herein by reference in its entirety.

FIELD

The present disclosure relates to health, beauty and cosmetics, more specifically, to formulations, methods and devices for periorbital skin rejuvenation.

BACKGROUND

People are increasingly concerned with physical appearance, which has led to numerous skin rejuvenation formulations, methods and devices.

However, many such formulations, methods and devices involve substances that are toxic (e.g., botulinum toxin), require injections (e.g., hyaluronic acid), require surgical procedures (e.g., blepharoplasty), are costly, are less-effective, and/or are otherwise less desirable.

There is thus a need in the art for improved formulations, methods and devices for periorbital skin rejuvenation.

BRIEF DESCRIPTION OF THE DRAWINGS

The accompanying drawings are included to provide a further understanding of the disclosure and are incorporated in and constitute a part of this specification, illustrate embodiments of the disclosure and together with the description serve to explain the principles of the disclosure.

SUMMARY

Figure 1A:
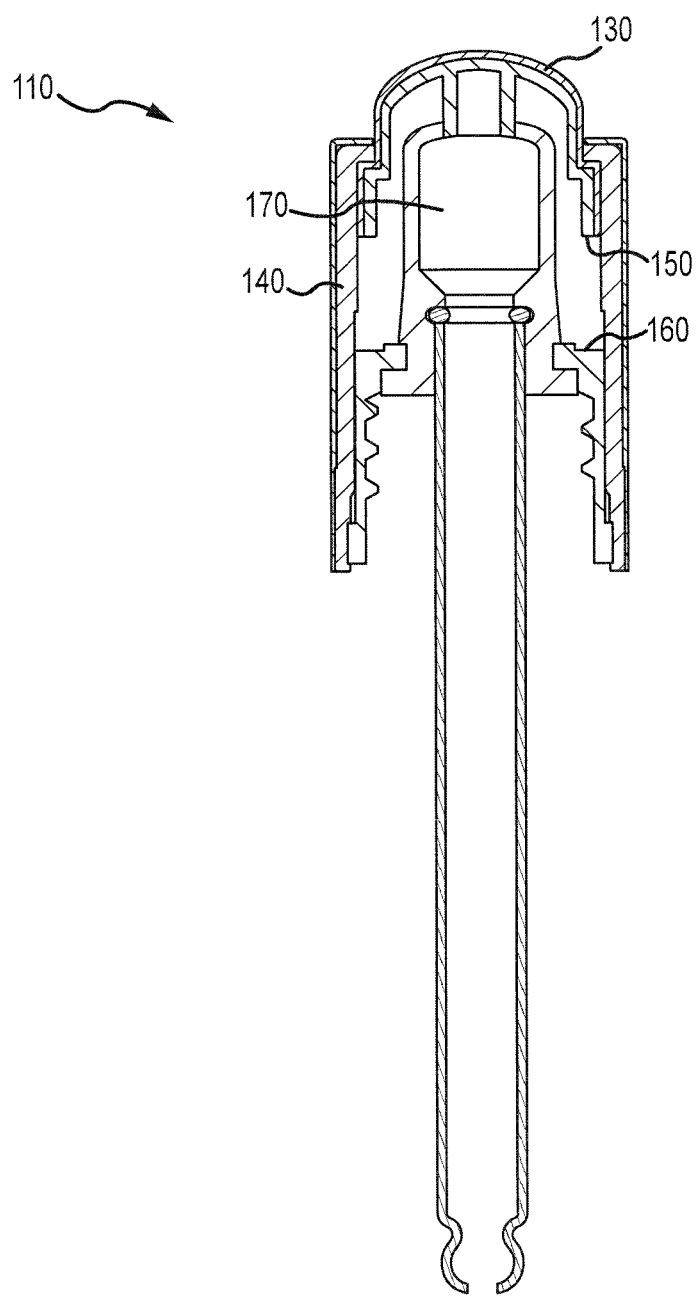
FIGS. 1A and 1B illustrate cross-sections of a delivery device in accordance with an example embodiment.

The present disclosure provides formulations, methods and devices for periorbital skin rejuvenation. A periorbital skin serum formulation in accordance with example embodiments comprises one or more skin-conditioning agents, one or more vitamins, and one or more catalysts.

DETAILED DESCRIPTION

The disclosure includes formulations, methods and devices for periorbital skin rejuvenation. Persons skilled in the art will readily appreciate that various aspects of the disclosure may be realized by any number of formulations, methods and devices configured to perform the intended functions. Stated differently, other formulations, methods and devices may be incorporated herein to perform the intended functions. Although the present disclosure may be in connection with various medical principles and beliefs, the present disclosure should not be bound by theory.

The term "approximately," as used in this specification and appended claims, refers to plus or minus five percent of the value given. The term "about," as used in this specification and appended claims, refers to plus or minus ten percent of the value given.

A periorbital skin serum formulation in accordance with example embodiments comprises one or more skin-conditioning agents, one or more vitamins, and one or more catalysts. Optional thickening agents, excipients, antimicrobial agents, preservatives, fragrances and colorants can also be included As used herein, a "skin-conditioning agent" is any substance, natural or synthetic, having one or more of the following properties: emollient, humectant, antioxidant, anti-aging, moisturizing, anti-inflammatory, enhanced sun protection factor (SPF), reduce free radical damage, assist cells in building collagens, glycosaminoglycans, elastin and proteoglycans, and the like.

A skin-conditioning agent in accordance with the present disclosure can comprise squalane or any other farnesene derivative, whether derived from vegetable sources (e.g., sugarcane (e.g., Neossance, Amyris), sugar beet, wheat), fruit sources (e.g., olive), animal sources (e.g., shark), or another source. Other skin-conditioning agents known in the art may be suitable for use in a periorbital skin serum of the present disclosure as well, including, but not limited to oil soluble plant extracts and esters including, iris pallida leaf cell extract (e.g., All Even Sweet Iris, Naolys), caprylic/capric triglyceride (e.g., All Even Sweet Iris, Naolys), C12-15 alkyl benzoate (e.g., All Q Plus, DSM Nutritional Products), octyldodecanol, octyldodecyl myristate, isocetyl stearate, phoenix dactylifera (date) seed extract, solanum lycopersicum seed oil, vaccinium macroparpon seed oil, helianthus annus seed oil, raspberry seed oil, simmondsia chinensis jojoba seed oil, argan oil, echium planagineum seed oil, aveena sativa (oat) oil, grape seed oil, sesame seed oil, coconut oil, pomegranate seed oil, coleus oil, lavender oil, avocado oil, panthenyl triacetate, ethyl linoleate, omega 3, 6, and 9 fatty acids, paraffin, isopropyl palmitate, dimethicone, to name a few. Notwithstanding the foregoing, those skilled in the art will readily appreciate that other skin-conditioning agents that perform the same or similar functions as those described supra may be used.

One or more skin-conditioning agents can be present in a periorbital skin serum in an amount of from about 50 to about 99.9 percent by weight, more preferably from about 90 to about 99.9 percent by weight, or most preferably about 99.5 percent by weight.

A vitamin in accordance with the present disclosure can comprise any form of vitamin E or derivative thereof (e.g., tocopheryl acetate (e.g., All Q Plus, DSM Nutritional Products), alpha tocopherol, tocopherol, tocopherol linoleate, tocopherol nicotinate, tocopheryl succinate tocottienols), any form of vitamin C or derivative thereof (e.g., tetrahexyldecyl ascorbate (e.g., BV-OSC, Barnet Products Corporation), ascorbyl palmitate, ascorbyl isostearate, ascorbic acid), any form of vitamin A or derivative thereof (e.g., retinol), any form of vitamin B or derivative thereof (e.g., niacinamade, niacin, folate), any form of vitamin K or derivative thereof, to name a few.

Other vitamins known in the art may be suitable for use in a periorbital skin serum of the present disclosure as well, and can be natural or synthetic. One or more vitamins can be present in a periorbital skin serum in an amount of from about 0.001 to about 5.0 percent by weight, more preferably from about 0.2 to about 1.0 percent by weight, or most preferably about 0.4 percent by weight.

A catalyst in accordance with the present disclosure is generally any substance that facilitates a process that enhances periorbital skin rejuvenation, and can comprise, to name just a few, an enzyme or a coenzyme, including, but not limited to ubiquinone (coenzyme Q10, oxidized form)

(e.g., All Q Plus, DSM Nutritional Products), ubiquinol (coenzyme Q10, reduced form), sirtuin, telomerase.

Other catalysts known in the art that perform the same or similar functions as those described supra may be suitable for use in a periorbital skin serum of the present disclosure as well, and can be natural or synthetic. One or more catalysts can be present in a periorbital skin serum in an amount of from about 0.001 to about 1.0 percent by weight, more preferably from about 0.05 to about 0.1 percent by weight, or most preferably about 0.08 percent by weight.

A periorbital skin serum in accordance with the present disclosure thus comprises squalane (sugarcane derived) in an amount of about 98.3 percent by weight, vitamin E (tocopheryl acetate) in an amount of about 0.2 percent by weight, vitamin C (tetrahexyldecyl ascorbate) in an amount of about 0.2 percent by weight, and ubiquinone (coenzyme Q10, oxidized form) in an amount of about 0.075 percent by weight.

Optional thickening agents, excipients, antimicrobial agents, preservatives, fragrances and colorants can also be included, for example isopropyl myristate, octyl myristate, cetearyl hexanoate, isononanoate, to name a few.

Thickening agents, excipients, antimicrobial agents, preservatives, fragrances and colorants can be present collectively in an amount of about 0.0025 percent by weight, up to about 0.04 percent by weight, or up to about 1.0 percent by weight.

A periorbital skin serum in accordance with the present disclosure can be applied topically, and can be a thin liquid, a gel, or a cream, to name a few. In general, an example embodiment of a periorbital skin serum is viscous enough to be easily applied to, and spread on, a periorbital skin surface yet not run or drop when applied to a vertical or near vertical periorbital skin surface.

The color of an example embodiment of a periorbital skin serum can be light yellow to yellow, or any other natural or artificial color. In some embodiments, the color matches that of a periorbital skin surface of a target consumer base, while in other embodiments, a periorbital skin serum is transparent or substantially transparent.

A periorbital skin serum in accordance with the present disclosure can be anhydrous or substantially anhydrous. An example embodiment of a periorbital skin serum can also be oil free or substantially oil free, and/or preservative free or substantially preservative free.

A periorbital skin serum in accordance with the present disclosure can comprise greater than 80 percent by weight natural ingredients, greater than 90 percent by weight natural ingredients, or greater than 98 percent by weight natural ingredients. As used herein, a "natural" refers to ingredients that are organic, present in natural foodstuffs, produced within the body, or devoid of synthetic substances.

A periorbital skin serum in accordance with the present disclosure was formulated comprising squalane (sugarcane derived), vitamin E (tocopheryl acetate), ubiquinone (coenzyme Q10, oxidized form), and C12-15 alkyl benzoate.

Another periorbital skin serum in accordance with the present disclosure was formulated comprising approximately 98.3 percent by weight squalane (sugarcane derived), approximately 0.2 percent by weight vitamin E (tocopheryl acetate), approximately 0.2 percent by weight vitamin C (tetrahexyldecyl ascorbate), approximately 0.1 percent by weight iris pallida leaf cell extract, approximately 0.075 percent by weight ubiquinone (coenzyme Q10, oxidized form), approximately 0.4 percent by weight caprylic/capric triglyceride, and approximately 0.725 percent by weight C12-15 alkyl benzoate. A periorbital skin serum as disclosed herein, can comprise, consist essentially of, or consist of, any or all of the foregoing in any combination.

A method of making a periorbital skin serum of the present disclosure comprises adding one or more skin-conditioning agents to a clean and sanitized container, and slowly adding the rest of the ingredients while mixing until completely uniform.

A method of using a periorbital skin serum of the present disclosure comprises applying from about 1 to about 5 drops, more preferably from about 2 to about 4 drops, or most preferably about 3 drops, of the periorbital skin serum to a periorbital skin surface daily, and massaging the periorbital skin serum into the periorbital skin surface. The procedure can be repeated one or more times daily, for example, once in the morning and once in the evening. In example embodiments, the periorbital skin surface is located lateral to an eye in the region of lateral canthal lines (i.e., crow's feet).

In various example embodiments, a method comprises applying a periorbital skin serum as described above, for a predetermined period of time (e.g., 1 week, 1 month, etc.).

A periorbital skin serum as described supra applied according to a method as described supra can provide for periorbital skin rejuvenation, for example, for a periorbital skin firmer, more elastic, more resistant and/or with less wrinkles.

A periorbital skin serum of the present disclosure can be delivered in any number of delivery devices. In an embodiment, a dropper engaged with a reservoir can be used. In such an embodiment, the dropper can be configured to draw up a preset volume of periorbital skin serum.

Figure 1B:
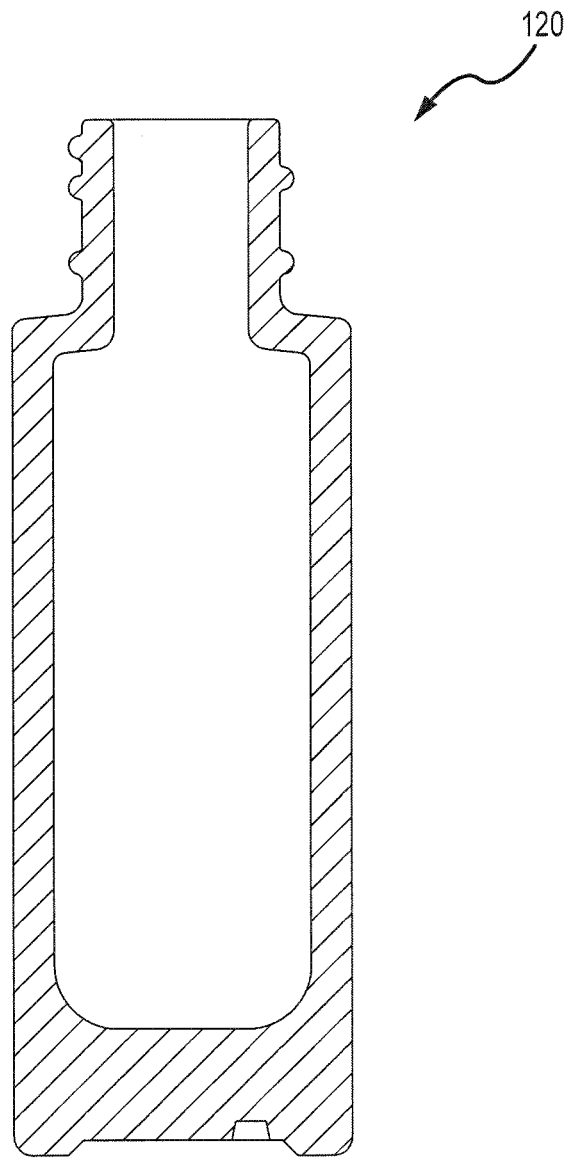

With reference to FIGS. 1A and 1B, cross-sections of a delivery device in accordance with an example embodiment are illustrated. The delivery device comprises a dropper 110 configured to engage with a reservoir 120. While dropper 110 is shown as being threadably engaged with reservoir 120, those skilled in the art will readily appreciate that the engagement may be comprise compression fit, snap, clip or the like.

Dropper 110 further comprises a press button or dial 130 configured to actuate a preset distance within a cap 140 of dropper 110 until a bottom edge 150 of press button or dial button 130 encounters a lip 160 within cap 140. Actuation of press button or dial 130 can compress a bulb 170 of dropper 110, to then draw up a preset volume of periorbital skin serum. In various embodiments, the preset distance between bottom edge 150 and lip 160 can be selected to corresponding to a desired volume of periorbital skin serum to be drawn up by dropper 110. A desired volume can be from about 1 to about 5 drops, more preferably from about 2 to about 4 drops, or most preferably about 3 drops (about 0.05 mL).

Reservoir 120 can have a volume of up to about 5 mL, 10 mL, 15 mL, 20 mL, or more. In example embodiments, the volume of reservoir 120 corresponds to a predetermined number of drops of periorbital skin serum to be applied to a periorbital skin surface over a predetermined period of time (e.g., 1 week, 1 month, etc.).

Either or both of dropper 110 and reservoir 120 can be comprised of any material, but in example embodiments, is comprised of a material that is impervious or substantially impervious with respect to a periorbital skin serum contained therein (e.g., glass).

Formulations, methods and devices are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The foregoing disclosure is merely illustrative of the present disclosure and is not intended to be construed as limiting the invention. Although one or more embodiments of the invention have been described, persons skilled in the art will readily appreciate that numerous modifications could be made without departing from the spirit and scope of the present disclosure. By way of example, a formulation in accordance with the present disclosure can comprise, consist essentially of, or consisting of, any combination of the ingredients described above. In addition, while the present disclosure has been described with reference to periorbital skin rejuvenation, persons skilled in the art will appreciate that the formulations, methods and devices herein can be applied to any other skin rejuvenation, for example, skin of the forehead, cheek, chin, neck, hands, etc. As such, it should be understood that all such modifications are intended to be included within the scope of the disclosure.

I claim:

1. A periorbital skin serum consisting of:
   vitamin E in an amount of about 0.2 percent by weight,
   vitamin C in an amount of about 0.2 percent by weight,
   ubiquinone in an amount of about 0.075 percent by weight, and
   skin-conditioning agents in an amount of about 99.5 percent by weight, wherein the skin-conditionings agents consist of squalane, iris pallida leaf cell extract, caprylic/capric triglyceride, and C12-15 alkyl benzoate.

2. The periorbital skin serum of claim 1, wherein the squalane is derived from sugarcane.

3. The periorbital skin serum of claim 1, wherein the periorbital skin serum comprises greater than 98 percent by weight natural ingredients.

4. The periorbital skin serum of claim 1, wherein the periorbital serum is anhydrous.

5. A method of using the periorbital skin serum of claim 1 comprising:
   providing the periorbital skin serum;
   applying from about 2 to about 4 drops of the periorbital skin serum to a periorbital skin surface twice daily; and
   massaging the periorbital skin serum into the periorbital skin surface.

6. The method of claim 5, wherein the squalane is derived from sugarcane.

* * * * *